United States Patent
Kuhn et al.

(10) Patent No.: US 6,538,154 B2
(45) Date of Patent: Mar. 25, 2003

(54) PROCESS FOR THE PREPARATION OF CINNAMIC ESTERS

(75) Inventors: Walter Kuhn, Holzminden (DE); Norbert Richter, Beverungen (DE); Lutz Walther, Holzminden (DE)

(73) Assignee: Haarmann & Reimer GmbH (DE)

( * ) Notice: Subject to any disclaimer, the term of this patent is extended or adjusted under 35 U.S.C. 154(b) by 0 days.

(21) Appl. No.: 10/013,204

(22) Filed: Dec. 7, 2001

(65) Prior Publication Data

US 2002/0082442 A1 Jun. 27, 2002

(30) Foreign Application Priority Data

Dec. 11, 2000 (DE) .......................................... 100 61 539

(51) Int. Cl.$^7$ ........................... C07C 69/76; C07C 63/64
(52) U.S. Cl. ........................................ 560/104; 562/495
(58) Field of Search ............................ 562/495; 560/104

(56) References Cited

U.S. PATENT DOCUMENTS 4,609,756 A  *  9/1986  Dorlars et al.
4,618,698 A     10/1986  Beitzke ........................ 560/60

OTHER PUBLICATIONS

Kalnin Zur Theorie der Perkin'schen Synthese. Uber den Mechanismus der Reaction, 1928, Helvetica Chimica Acta, 11, pp. 977–1003.*

Weber, Prebiotic Sugar Synthesis: Hexose and Hydroxy Acid Synthesis from Glyceraldehyde Catalyzed by Iron(III) Hydroxide Oxide, 1992, Journal of Molecular Evolution, 35(1), pp. 1–6. Abstract Only.*

Solomons, Organic Chemistry, 5th edition, 1992, John Wiley & Sons, Inc., New York, pp. 777–778.*

Chem. Abstract, 1976 85:14285h & JP 51015026.

Chem. Abstract, 95:95470 & JP 56026197.

Houben–Weyl, Methoden der organische chemie, vol. III/3, (month unavailable) 1952, p. 443, "Herstellung von Carbonsäuren durch Kohlenstoffverkettung".

J. Chem. Soc., 31, (month unavailable) 1877, pp. 388–427, W. H. Perkin, "On the Formation Of Coumarin and of Cinnamic and of other Analogous Acids from the Aromatic Aldehydes".

Ullmann's Encyclopedia of Industrial Chemistry, 6$^{th}$ edition electronic release, 1999, vol. A 24, Cinnamic Acid—Production, Dorothea Garbe.

Helv. Chim. Acta. 11, (month unavailable) 1928, pp. 977–1003, Paul Kalnin, "Zur Theorie der Perkin'schen Synthese Über den Mechanismus der Reaktion".

Org. Reactions I, (month unavailable) 1942, pp. 210–265, John R. Johnson, "The Perkin Reaction & Related Reactions".

Claisen–Schmidt Reaction; (Ber. 23,) (month unavailable) 1890, pp. 976–978, L. Claisen, "Zur Darstellung der Zimmtsäure und ihrer Homologen".

* cited by examiner

Primary Examiner—Johann Richter
Assistant Examiner—Paul A. Zucker
(74) Attorney, Agent, or Firm—Pendorf & Cutliff

(57) ABSTRACT

The present invention relates to a process for the synthesis of cinnamic esters and/or cinnamic acids by condensation of aldehydes with carboxylic anhydrides, using iron(II) salts as catalyst.

14 Claims, No Drawings

PROCESS FOR THE PREPARATION OF CINNAMIC ESTERS

FIELD OF THE INVENTION

The present invention relates to a process for the synthesis of cinnamic esters and substituted cinnamic esters by condensation of aldehyde(s) with carboxylic anhydride(s) catalysed by iron(III) salts.

BACKGROUND OF THE INVENTION

The direct route to cinnamic esters is possible via the condensation of aromatic aldehydes with acetic esters (Claisen-Schmidt reaction; (Ber. 23, 976 (1890)) and can be carried out in the presence of metallic sodium. Ullmanns Encyclopedia of Industrial Chemistry 6$^{th}$ Edition, Electronic Release, 1999, Vol. A 24, 231–239 and DE 3422412 describe the condensation of benzaldehyde with acetic esters with alkoxide catalyst in alcohol.

In said cases, the catalyst is used in an at least equimolar amount relative to the benzaldehyde and thus significantly increases the preparation costs of the cinnamic ester. Handling of the catalyst is associated with a high hazard potential.

The Perkin reaction (Perkin, J. Chem. Soc. 31,388 (1877)) likewise offers the possibility of preparing cinnamic acid and cinnamic esters by reacting an aromatic aldehyde, such as benzaldehyde, and acetic anhydride with sodium acetate catalysis. Houben Weyl, Methoden der organischen Chemie [Methods of organic chemistry], 4th Ed., Vol. VIII/3, p. 443, Georg Thieme Verlag Stuttgart, 1952 describes the reaction of benzaldehyde with acetic anhydride and sodium acetate in a molar ratio of 1:1.56:0.65 under reflux/16 h. Work-up from water gives cinnamic acid in a yield of 57%.

By heating for 24 hours or by adding pyridine, it is possible to increase the yield to 70–75%.

JP A 76/15,026; CA 1976, 85:14285h describe the reaction of benzaldehyde with acetic anhydride and sodium acetate in a molar ratio of 1:0.5:0.5 and a reaction temperature of 160° C./1 h. The yield of cinnamic acid is 30% under these conditions. If sodium acetate is replaced with potassium phosphate or sodium phosphate, the yield increases to 46%.

J. R. Johnson, Org. Reactions I. 210 (1942) describes the reaction of 0.2 mol of benzaldehyde and 0.3 mol of acetic anhydride using 0.12 mol of potassium acetate. The mixture is refluxed for 5 hours at 170° C. The reaction mixture is poured onto 1,200 ml of water. Unreacted benzaldehyde is isolated by steam distillation. Activated carbon is added and the mixture is heated. Following filtration, 12–14 ml of conc. hydrochloric acid are added at elevated temperature, and the system is cooled. The precipitated crystals are filtered off with suction and dried. 16–18 g of cinnamic acid are obtained; the yield is 55–60% based on the amount of benzaldehyde used.

P. Kalnin, Helv. Chim. Acta 11, 977 (1928) describes various salts as catalysts. 1 mol of benzaldehyde and 1.5 mol of acetic anhydride are refluxed at 180° C. for 8 hours with 0.65 mol of catalyst. The yields of cinnamic acid are, following work-up, for potassium acetate 72%, for potassium carbonate 59%, for sodium carbonate 40%, for sodium acetate 39%, for sodium phosphate 36%, for potassium phosphate 20% and for potassium sulphide 32%. As well as potassium and sodium salts, amines are also possible as catalysts. For 0.33 mol of triethylamine, the yield is 19%.

A disadvantage of said process variants is the large amount of catalyst used, which makes the product expensive and hinders the reaction and also the work-up.

SUMMARY OF THE INVENTION

Therefore, an object of the present invention is to find a low-cost catalyst which, in small amounts, permits the preparation of cinnamic esters or cinnamic acid by condensation of aldehyde(s) with carboxylic anhydride(s) in the presence of a catalyst.

A process for the preparation of cinnamic esters and/or cinnamic acid by condensation of aldehydes with carboxylic anhydrides in the presence of a catalyst has been found, which is characterized in that catalysts, or catalyst mixtures, containing iron(III) salts are used.

DETAILED DESCRIPTION OF THE INVENTION

Cinnamic esters and/or cinnamic acid for the process according to the present invention are generally compounds of the formula (I)

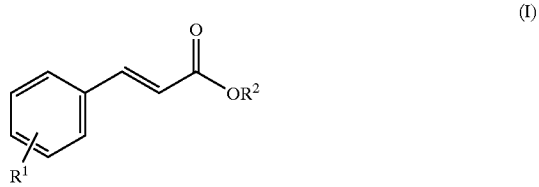

in which

R$^1$ independently of one another are hydrogen, alkyl, cycloalkyl, aryl, aralkyl, dialkyamino, diarylamino, halogen, alkoxy, aryloxy, cycloalkoxy, aralkoxy, alkoxycarbonyl, aryloxycarbonyl, alkylcarbonyloxy, alkylthio, arylthio, cycloalkylthio or aralkylthio, alkyl radicals, including those in the oxygen-containing or sulfur-containing substituents, have 1–16, preferably 1–10, particularly preferably 1–4 carbon atoms, such as methyl, ethyl, propyl, isopropyl, butyl, isobutyl, cycloalkyl radicals, including those in the oxygen-containing or sulfur-containing substituents, are those with 4–8, preferably 5–6, carbon atoms arranged in the ring, which may carry one or two methyl or ethyl groups, such as cyclobutyl, cyclopentyl, cyclohexyl, cycloheptyl, cyclooctyl, methylcyclopentyl or methylcyclohexyl, aryl radicals, including those in the oxygen-containing or sulfur-containing substituents, may be phenyl, naphthyl, anthryl or diphenyl, preferably phenyl, in which R$^1$ is hydrogen, methyl, ethyl, methoxy, ethoxy or phenoxy and R$^2$ are hydrogen or C$_1$–C$_8$-alkyl.

The iron(III) salts which can be used are, for example, iron acetate, iron subcarbonate, iron oxide, iron oxide hydrate, iron oxalate, iron lactate or iron tartrate.

According to the present invention, preference is given to using aromatic aldehydes. Examples of such aldehydes which can be used according to the present invention, which may be mentioned are, for example, benzaldehyde and substituted benzaldehydes of the formula II,

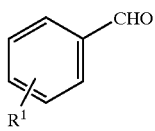 (II)

in which $R^1$ has the meaning given above.

Suitable carboxylic anhydrides are $C_2$–$C_4$-carboxylic anhydrides. Examples of anhydrides which can be used are acetic anhydride, propionic anhydride and butyric anhydride.

The reaction according to the present invention is generally carried out by heating the components aromatic aldehyde, carboxylic anhydride and catalyst, and distilling off a carboxylic acid/carboxylic anhydride mixture at the same time.

Carboxylic anhydride is used in an amount of 1–5 mol of the aromatic aldehyde, preferably in an amount of 1.5–2.5 mol. Excess aromatic aldehyde can be recovered by distillation when the reaction is complete and used for a new batch.

The reaction is carried out at a temperature of from 100° C. to 200° C., preferably at 120° C. to 170° C. The process according to the present invention can be carried out at atmospheric pressure. The reaction is advantageously carried out under a protective gas, for example under nitrogen, in order to exclude water (atmospheric moisture), carbon dioxide and oxygen.

Where benzaldehydes and acetic anhydride are used, the following mixture can, for example, be obtained:

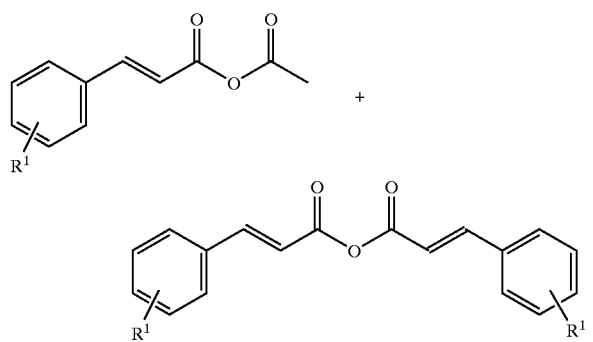

The resulting anhydride can be converted in the presence of alcohols to give esters. Preference is given to using alcohols of the formula (II):

$R^2$—OH (II)

where $R^2$ is hydrogen or $C_1$–$C_8$-alkyl.

The alcohol can be used in an amount of 1–25 mol per mole of benzaldehyde, preferably 1.5–5 mol.

Where benzaldehyde and acetic anhydride are used, the reaction below can, for example, accordingly be carried out:

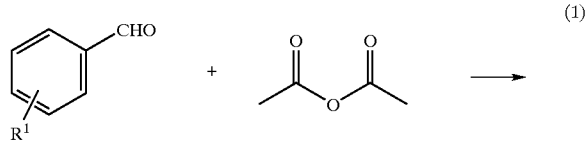 (1)

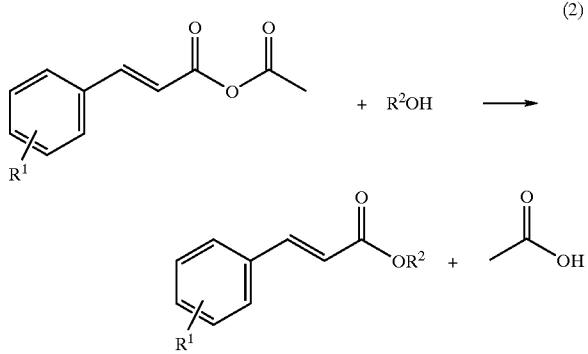

$R^1$ and $R^2$ here have the meanings already given above.

Cinnamic alkyl esters are used in particular in the perfume and essence industry (Ullmanns Encyclopädie der technischen Chemie [Ullmanns Encyclopaedia of Industrial Chemistry], 4th edition, volume 24, page 592 (1983)).

The anhydride formed can also be reacted in the presence of water and cinnamic acid be prepared.

Alternatively, the acid can also be prepared from the ester formed. This is preferably carried out by hydrolysis. The hydrolysis can either be carried out in acidic or alkaline conditions. In this way, cinnamic acid can be produced from the cinnamic esters formed according to the above reaction schemes.

The hydrolysis of the ester is carried out in accordance with customary methods (Houben-Weyl, volume VIII, page 418) and is preferably carried out under alkaline conditions. Examples of bases, which can be used, are aqueous sodium hydroxide solution or aqueous potassium hydroxide solution, preferably aqueous potassium hydroxide solution. The base is used in an amount of 1–5 mol, preferably 1.5–25 mol per mole of the ester present in the ester mixture. The hydrolysis is carried out at a temperature of 20–150° C., preferably 60–120° C., and more preferably at 90–110° C. The free cinnamic acid is isolated from the hydrolysis mixture, for example, by acidification.

Cinnamic acid and substituted cinnamic acids are used widely, for example, for the preparation of esters for the perfume and essence industry. Sodium cinnamate is also a corrosion in hibitor (Ullmann, volume 24, page 592 (1983)). Cinnamic acid is also an intermediate for the preparation of phenylalanine (JP 81/26197), cited in accordance with Chem. Abstr. 95, 95470 b.

EXAMPLES

Example 1

Preparation of Methyl Cinnamate

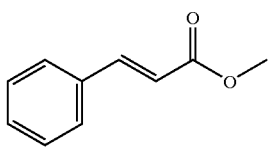

A mixture of 1,696 g (16 mol) of benzaldehyde, 2,448 g (24 mol) of acetic anhydride and 36 g (0.2 mol) of iron subcarbonate are refluxed at 145° C. for 0.5 hours. The head temperature drops to 120° C. Distillation is carried out over 13 hours at atmospheric pressure and at a still temperature of from 120° C. to 170° C. 816 g (8 mol) of acetic anhydride are then added, and the mixture is again distilled over 6 hours at a still temperature of from 150° C. to 170° C. The mixture is cooled to a still temperature of 150° C. and distilled at a vacuum down to 50 mbar. In total, 2,589 g of an acetic acid/acetic anhydride mixture are distilled off.

1,200 g of toluene are added and then, at a still temperature of 30° C. to 78° C., a mixture of 822 g of methanol (26 mol) and 200 g (2 mol) conc. sulfuric acid is metered in. The mixture is refluxed for 10 hours.

1,000 g of water are added to the crude mixture and the phases are separated. The organic phase is washed with 600 ml of saturated sodium carbonate solution. The washed organic phase is distilled in vacuo over a 14-plate column. At 60° C. to 63° C./10 mbar, 208 g of benzaldehyde pass over. 1,778 g of methyl cinnamate (GC purity 97.8%) are obtained at 91° C./1 mbar. The theoretical yield is 68%, based on the benzaldehyde used.

Example 2

Preparation of Ethyl Cinnamate

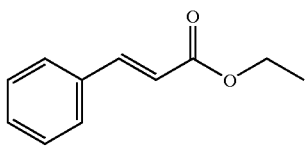

473 g (4.46 mol) of benzaldehyde and 10 g (0.05 mol) of iron subcarbonate are introduced at 165° C. 798 g (7.82 mol) of acetic anhydride are metered in at 160–165° C. over a period of 20 hours, and the mixture is simultaneously distilled at a head temperature of 122° C. Following the metered addition, the mixture is heated to 165° C. and distilled at a vacuum down to 50 mbar. In total, 607 g of an acetic acid/acetic anhydride mixture are distilled off.

Then, at a still temperature of 130° C., a mixture of 340 g of ethanol (7.39 mol) and 56 g (0.54 mol) conc. sulfuric acid is metered in. Following the metered addition, 2,074 g of ethyl acetate/ethanol mixture are distilled off at 85–87° C. under an increasing vacuum down to 500 mbar.

258 g of a 10% strength NaOH solution are added to the crude mixture, and the phases are separated. The organic phase is admixed with 3 g of acetic acid and distilled in vacuo over a 14-plate column.

At 75° C. to 101° C./20 mbar, 570 g of benzaldehyde pass over. 424 g of ethyl cinnamate (GC purity 99.5%) are obtained at 117–122° C./1 mbar.

The theoretical yield is 54% based on the benzaldehyde used.

Example 3

Preparation of Methyl 4-Methylcinnamate

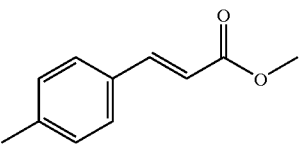

A mixture of 1,070 g (8.9 mol) of 4-methylbenzaldehyde and 20 g (0.1 mol) of iron subcarbonate is heated to 165° C. Over the course of 24 hours, 2,040 g (20 mol) of acetic anhydride are metered in at a still temperature of from 165° C. to 170° C. At the same time, a mixture of acetic acid/acetic anhydride is distilled off at a head temperature of from 118° C. to 123° C. A vacuum down to 50 mbar is then applied. In total, 1,730 g of acetic acid/acetic anhydride mixture distill off. As the still temperature drops from 130° C. to 75° C., a mixture of 1,140 g of methanol (35.6 mol) and 220 g (2.1 mol) of conc. sulfuric acid is metered in over the course of 2 hours, and a methyl acetate/methanol mixture is distilled off at the same time. Following the metered addition, a vacuum down to 500 mbar is applied. A total of 420 g of methyl acetate/methanol mixture are distilled off.

The crude mixture is washed at 50° C. with 480 g of 10% strength NaOH solution. The crude product (1,452 g) is treated with 8 g of acetic acid for the distillation and distilled in vacuo over a 15-plate column.

At 111° C./4 mbar, 100 g of 4-methylbenzaldehyde pass over. 820 g of methyl 4-methylcinnamate (GC purity 98%) are obtained at 110° C./1 mbar. The theoretical yield is 52% based on the 4-methylbenzaldehyde used.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of cinnamic esters and/or cinnamic acids comprising the step of condensing aldehydes with carboxylic anhydrides in the presence of a catalyst or a catalyst mixture, wherein said catalyst, or catalyst mixture, comprise iron (III) salts and wherein said iron (III) salts or mixtures are selected from the group consisting of iron acetate, iron carbonate, iron oxide, iron oxide hydrate, iron oxalate, iron lactate and iron tartrate.

2. A process according to claim 1, wherein said amount of iron(III) salts is 0.0001–0.2 mole equivalents based on the amount of aldehyde.

3. A process according to claim 1, wherein said aldehydes are aromatic aldehydes.

4. A process according to claim 3, wherein said aromatic aldehydes are benzaldehydes or substitutes benzaldehydes.

5. A process according to claim 1, wherein said carboxylic anhydride is acetic anhydride.

6. A process according to claim 1, wherein said carboxylic anhydride is used in amounts of 1–5 mol per mole of aldehyde.

7. A process according to claim 1, wherein the process is carried out at temperatures of 100–200° C.

8. A process according to claim 1, wherein the process is carried out with the exclusion of oxygen, water and carbon dioxide.

9. A process according to claim 1, wherein the process is carried out in the presence of a protective gas.

10. A process according to claim 1, wherein the anhydride formed by the reaction of aldehyde and carboxylic anhydride is reacted in the presence of alcohols to give cinnamic ester.

11. A process according to claim 1, herein the anhydride formed by reacting the aldehyde and carboxylic anhydride is reacted with water to give cinnamic acid.

12. A process according to claim 1, wherein the ester is converted to cinnamic acid by acidic or alkaline hydrolysis.

13. A process according to claim 12, wherein sodium hydroxide solution or potassium hydroxide solution are used.

14. A process according to claim 13, wherein said hydroxide solution is used in an amount of 1–5 mol per mole of ester.

* * * * *